United States Patent [19]

Hinchcliffe

[11] Patent Number: 5,403,329
[45] Date of Patent: Apr. 4, 1995

[54] INSTRUMENT FOR CLOSING TROCAR PUNCTURE WOUNDS

[75] Inventor: Peter W. J. Hinchcliffe, Orange, Conn.

[73] Assignee: United States Surgical Corporation, Norwalk, Conn.

[21] Appl. No.: 216,073

[22] Filed: Mar. 21, 1994

Related U.S. Application Data

[63] Continuation of Ser. No. 950,073, Sep. 23, 1992, abandoned.

[51] Int. Cl.$^6$ ............................................. A61B 17/00
[52] U.S. Cl. ..................... 606/147; 606/139; 606/144; 112/169; 112/80.03
[58] Field of Search .............. 606/139, 144, 145, 147, 606/148, 146, 150, 210, 211, 205–208, 184–187; 112/80.03, 169

[56] References Cited

U.S. PATENT DOCUMENTS

| | | |
|---|---|---|
| 1,037,864 | 9/1912 | Carlson et al. . |
| 1,449,087 | 3/1923 | Bugbee . |
| 1,822,330 | 9/1931 | Ainslie . |
| 2,108,206 | 2/1938 | Meeker ............................ 606/148 |
| 2,213,830 | 9/1940 | Anastasi . |
| 2,549,731 | 4/1951 | Wattley ........................... 606/206 |
| 2,579,192 | 12/1951 | Kohl ................................. 112/169 |
| 2,601,564 | 6/1952 | Smith . |
| 2,737,954 | 3/1956 | Knapp . |
| 3,090,386 | 5/1963 | Curtis . |
| 3,168,097 | 2/1965 | Dormia . |
| 3,470,875 | 10/1966 | Johnson . |
| 3,807,407 | 4/1974 | Schweizer . |
| 3,871,379 | 3/1975 | Clarke . |
| 3,901,244 | 8/1975 | Schweizer . |
| 3,946,740 | 3/1976 | Bassett . |
| 4,103,690 | 8/1978 | Harris . |
| 4,493,323 | 1/1985 | Albright et al. ................. 606/144 |
| 4,557,265 | 12/1985 | Anderson . |

(List continued on next page.)

FOREIGN PATENT DOCUMENTS

| | | |
|---|---|---|
| 0140557 | 5/1985 | European Pat. Off. . |
| 0542126 | 5/1993 | European Pat. Off. . |
| 1093329 | 5/1984 | U.S.S.R. ............................ 606/145 |
| 8503858 | 3/1985 | WIPO . |
| 9204869 | 4/1992 | WIPO . |

OTHER PUBLICATIONS

REMA Brochure, REMA-Medizintechnik GmbH, 1992.
European Patent Office Search Report dated Jan. 24, 1994, for EP application No. 93115173.

*Primary Examiner*—Stephen C. Pellegrino
*Assistant Examiner*—Jeffrey A. Schmidt

[57] ABSTRACT

An instrument for closing trocar puncture wounds having a handle assembly with a stationary portion and a movable portion; an elongated portion attached at a proximal end thereof to the stationary portion of the handle assembly; and needle deploying means associated with the elongated portion. The needle deploying means includes: an actuator member having a proximal end operably connected to the movable portion of the handle assembly and a distal end disposed adjacent a distal end of the elongated portion, the actuator member being slidable between a first position and a second position; and at least one needle carrier member mounted adjacent the distal end of the actuator member, the needle carrier being slidable relative to the actuator member upon movement thereof, between a retracted position substantially within the elongated portion and an extended position substantially without the elongated portion. The instrument of the present invention also provides a novel suture retaining feature including at least one elongated channel disposed along the actuator member such that a length of suture may be received and retained within the channel and carried therein, between the elongated portion and the actuator member.

22 Claims, 5 Drawing Sheets

U.S. PATENT DOCUMENTS

| | | | |
|---|---|---|---|
| 4,597,390 | 7/1986 | Mulhollan et al. | |
| 4,602,635 | 7/1986 | Mulhollan et al. | |
| 4,614,187 | 9/1986 | Mulhollan et al. | |
| 4,621,640 | 11/1986 | Mulhollan et al. | |
| 4,635,638 | 1/1987 | Weintraub et al. | |
| 4,676,243 | 6/1987 | Clayman | |
| 4,827,931 | 5/1989 | Longmore | |
| 4,830,002 | 5/1989 | Semm | 606/207 |
| 4,836,205 | 6/1989 | Barrett | |
| 4,841,885 | 6/1989 | Santino | 112/80.03 |
| 4,852,568 | 8/1989 | Kensey | |
| 4,890,615 | 1/1990 | Caspari et al. | |
| 4,907,590 | 3/1990 | Wang et al. | 606/139 |
| 4,923,461 | 5/1990 | Caspari et al. | |
| 4,935,027 | 6/1990 | Yoon | |
| 4,957,498 | 9/1990 | Caspari et al. | |
| 4,963,147 | 10/1990 | Agee et al. | |
| 4,971,067 | 11/1990 | Bolduc et al. | |
| 4,986,825 | 1/1991 | Bays et al. | |
| 5,037,433 | 8/1991 | Wilk et al. | |
| 5,047,039 | 9/1991 | Avant et al. | |
| 5,109,780 | 5/1992 | Slouf et al. | 112/169 |
| 5,129,912 | 7/1992 | Noda et al. | 606/148 |
| 5,152,769 | 10/1992 | Baber | |
| 5,217,471 | 6/1993 | Burkhart | |

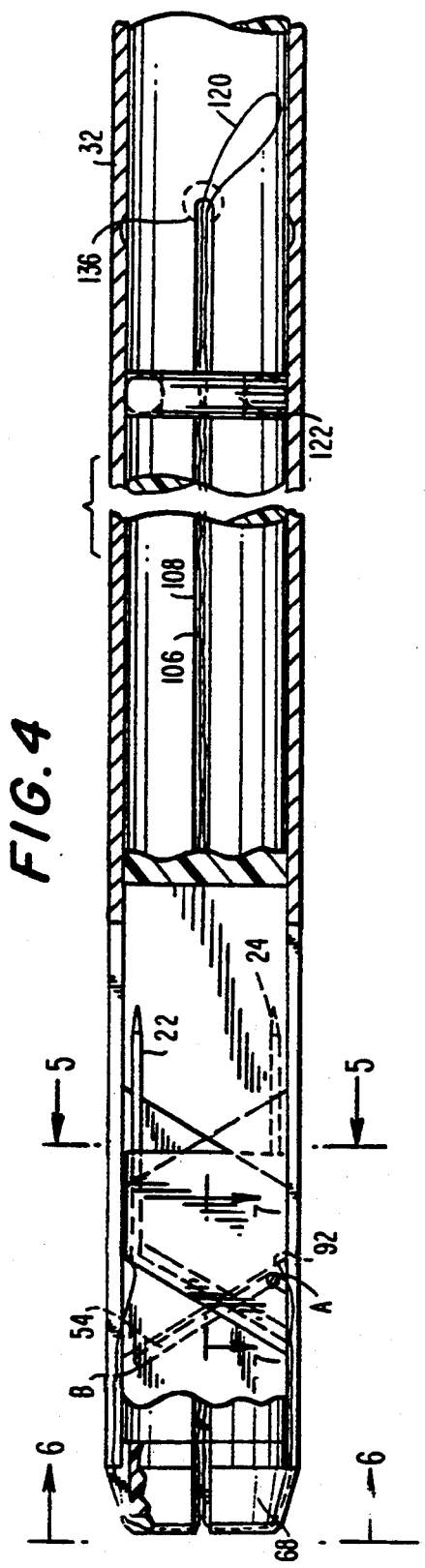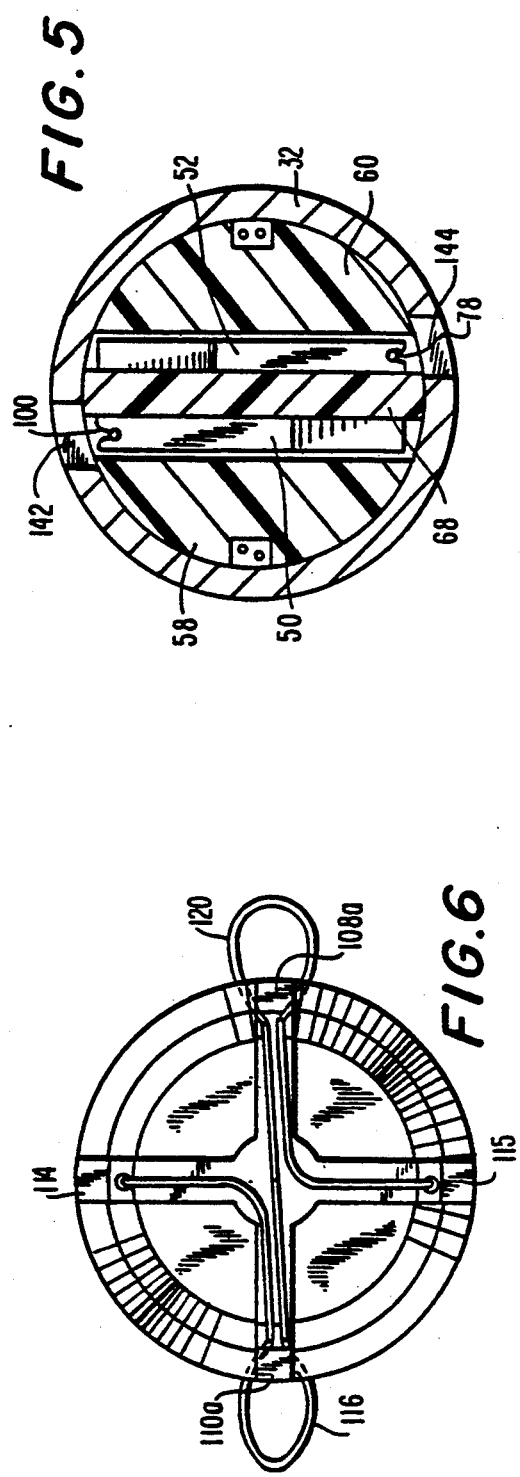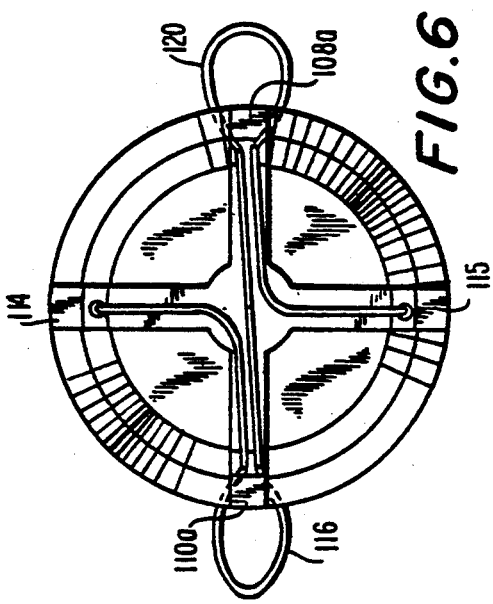

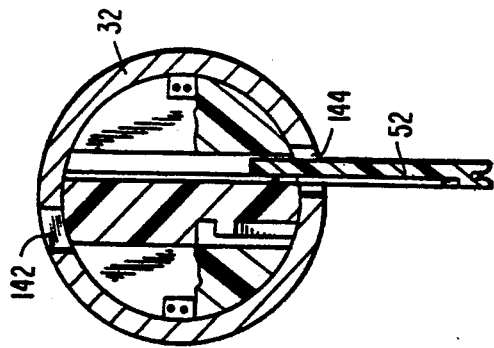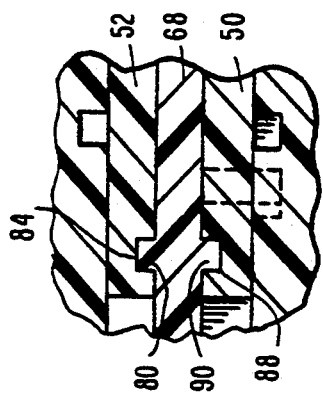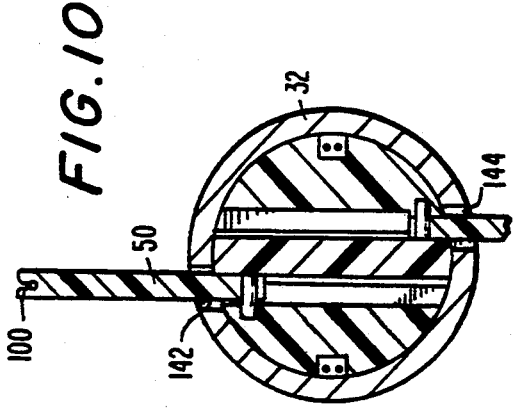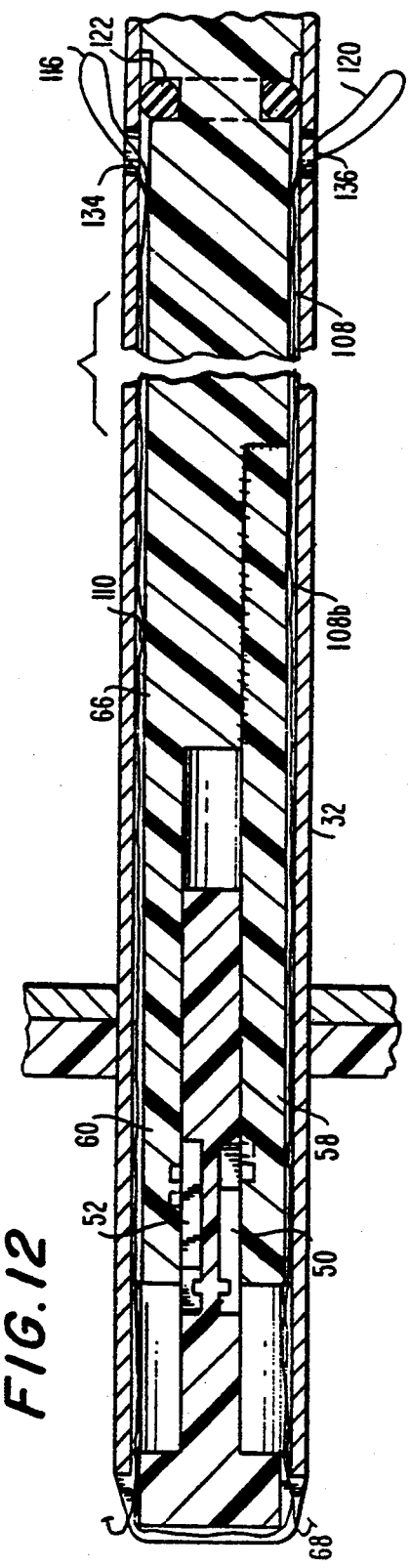

INSTRUMENT FOR CLOSING TROCAR PUNCTURE WOUNDS

This is a continuation of application Ser. No. 07/950,073, filed on Sep. 23, 1992, now abandoned.

BACKGROUND OF THE INVENTION

1. Field of the Invention

This invention relates to instruments for suturing puncture wounds and more particularly to instruments for closing trocar puncture wounds formed during endoscopic surgical procedures.

2. Description of the Related Art

With laparoscopic and endoscopic surgery, a small incision or puncture is made in the patient's body to provide access for a tube or a cannula device. Once extended into the patient's body, the cannula allows for insertion of various surgical instruments such as scissors, dissectors, retractors, or biopsy instruments to perform diagnostics and/or surgery. Upon completion of the surgical procedure, the remaining trocar wound may require some attention, e.g., in the form of placing sutures to close the wound. In cases where sutures formed at the surface are not effective in properly closing the wound it may be desirable to close the wound from within.

Devices which form sutures from within the urethra are known. In one such device, the device is inserted into the urethra and pivotally deploys needles from which sutures are subsequently pulled through the side walls of the urethra. See, for example, Soviet Patent SU 1093329.

Accordingly, a need exists, for an improved instrument which provides better deployment of the needles, more efficient storing of the suture within the device for more reliable operation and increased capacity for storing sutures of varying lengths therein.

SUMMARY OF THE INVENTION

The present invention provides a novel instrument for closing trocar puncture wounds and includes a lightweight and easy to use instrument which may be operated quickly and efficiently. The instrument is easy to manufacture and is usable with currently available trocar cannulas.

The instrument includes a handle assembly having a stationary portion and a movable portion; an endoscopic portion attached at a proximal end thereof to the stationary portion of the handle assembly; and needle deploying means associated with the endoscopic portion. The needle deploying means includes: an actuator member having a proximal end operably connected to the movable portion of the handle assembly and a distal end disposed adjacent a distal end of the endoscopic portion. The actuator member is slidable between a first position and a second position and engages at least one needle carrier member adjacent the distal end of the actuator member. The needle carrier is slidable relative to the actuator member upon movement thereof, between a retracted position substantially within the endoscopic portion and an extended position substantially outside the endoscopic portion.

In a preferred embodiment, a pair of needle carriers are provided such that they deploy to their extended position from diametrically opposed sides of the endoscopic portion as a result of longitudinal movement of the actuator member.

Means including an elongated plug member having transverse grooves formed therein for receiving and guiding the needle carriers relative to the actuator member may also be provided. Alternatively, a boss portion may be provided in the transverse groove to cooperate with slots formed in the needle carriers.

The instrument of the present invention also provides a novel suture retaining feature including at least one elongated channel disposed longitudinally along the actuator member such that a length of suture may be received and retained within the channel and carried therein between the endoscopic portion and the actuator member.

BRIEF DESCRIPTION OF THE DRAWINGS

Preferred embodiments of the invention are described hereinbelow with reference to the drawings wherein:

FIG. 3 is a perspective view of the suture arrangement within the instrument of FIG. 1;

FIGS. 4 is a cross-sectional view of the instrument of FIG. 1 showing the needle carriers in their retracted position;

FIG. 5 is a cross-sectional view taken along line 5—5 of FIG. 4;

FIG. 6 is a end view taken along line 6—6 of FIG. 4;

FIG. 7 is an enlarged fragmentary cross-sectional view taken along line 7—7 of FIG. 4;

FIG. 10 is a cross-sectional view taken along line 10—10 of FIG. 8;

FIG. 11 is a cross-sectional view taken along line 11—11 of FIG. 8; and

FIG. 12 is a cross-sectional view taken along line 12—12 of FIG. 8.

DETAILED DESCRIPTION OF THE PREFERRED EMBODIMENTS

Figure 1:
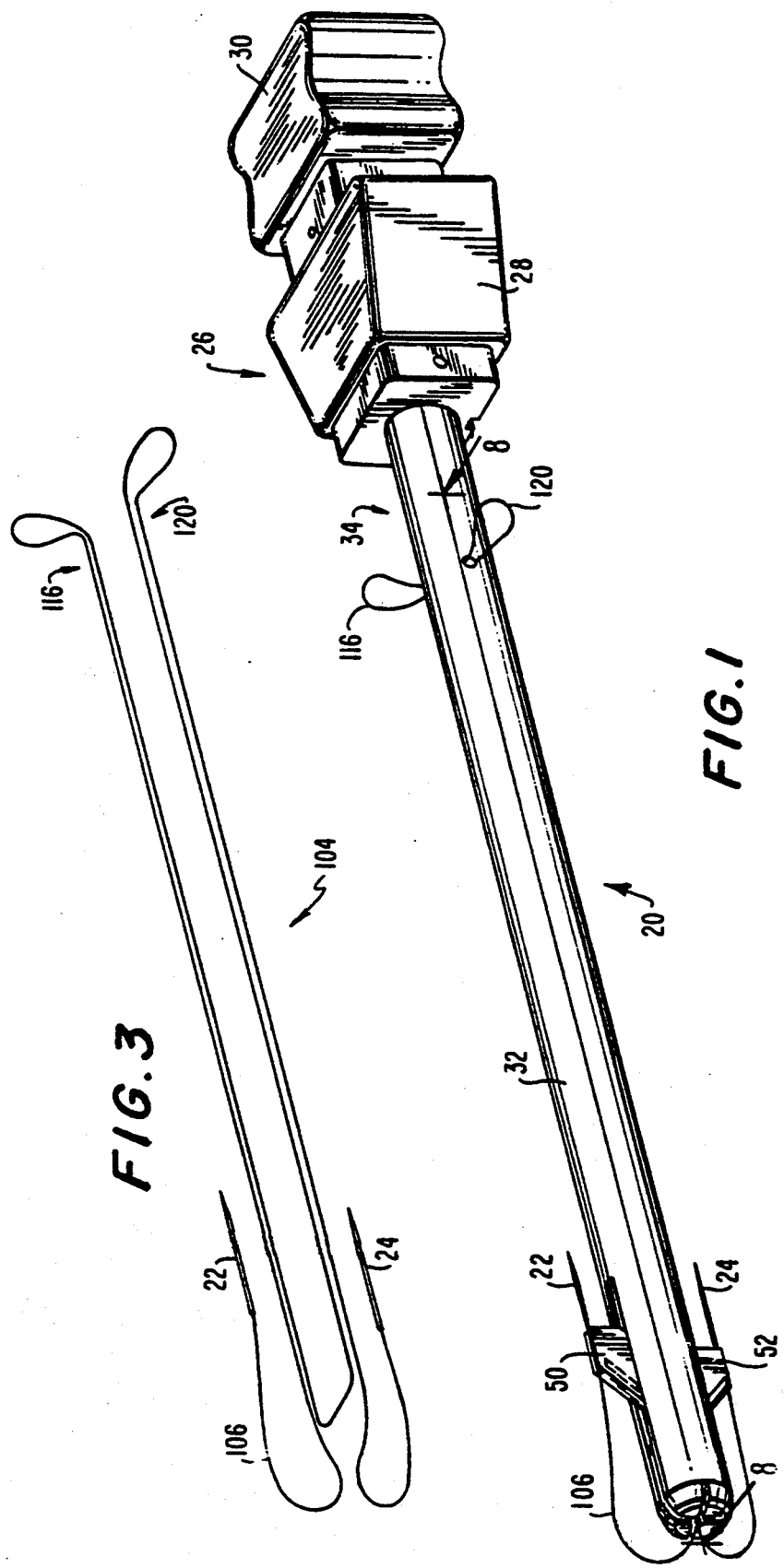
FIG. 1 is a perspective view of the instrument of the present invention.
Figure 2:
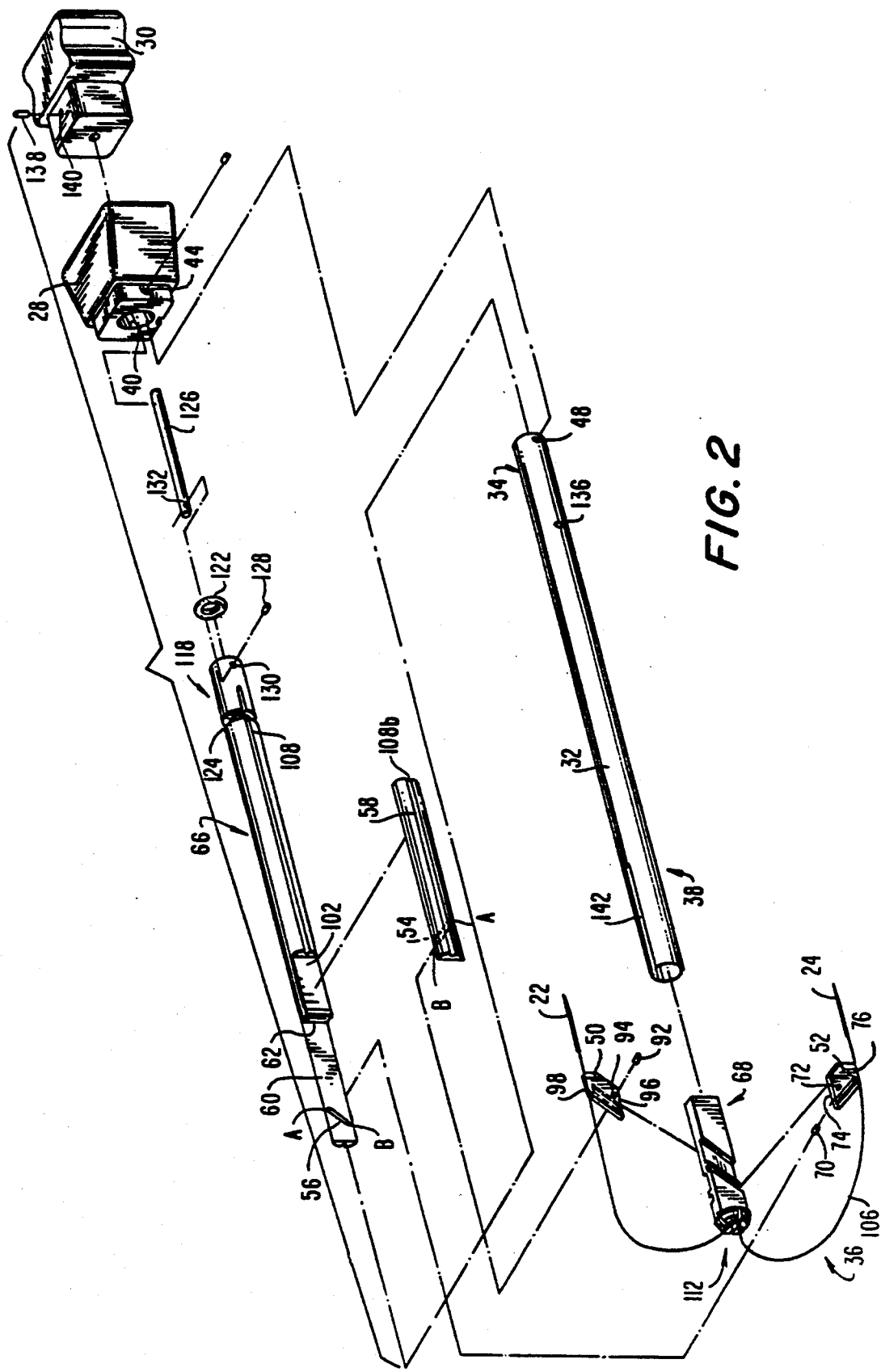
FIG. 2 is an exploded view with parts separated of the instrument of FIG. 1.

Referring initially to FIGS. 1-3, one embodiment of an instrument for closing puncture wounds in accordance with the present invention is shown generally at 20. This instrument 20 is particularly adapted for driving a pair of needles 22 and 24 from within the endoscopic cavity of a patient into the peripheral tissue adjacent an endoscopic puncture wound and placing a suture therein. However, clearly, instruments which utilize more or less than two needles are within the scope of the invention.

Generally, closure device 20 includes handle assembly 26 having stationary handle portion 28 and movable handle portion 30; an endoscopic portion including elongated tubular body 32 connected at a proximal end 34 to stationary handle 28; and needle deployment assembly 36 (FIG. 2) mounted adjacent distal end 38 of elongated body portion 32. Except where noted otherwise, the materials utilized in the components of the instrument generally include such materials as polycarbonate for housing sections and related components, and stainless steel, particularly for components which transmit forces. One preferred material is a polycarbonate material available from General Electric Company under the trade name LEXAN. Other specific preferred materials such as nylon or glass filled nylon (for strength) may also be utilized. However, equivalent alternative materials will readily come to the mind of those skilled in the art.

Referring to FIG. 2, the components of instrument 20 and their relative assembly are illustrated. These components include an elongated body portion 32, a needle deployment assembly 36, and a longitudinally slidable actuator member 66. Elongated body portion 32 is a longitudinal sheath assembled with stationary handle 28 by inserting proximal end 34 of elongated body portion 32 into bore 40 formed in stationary handle 28. Any suitable mounting method may be utilized, such as by pin 42 being inserted into hole 44 on the side of stationary handle shank 46 and through hole 48 located at proximal end 34 of elongated body portion 32. The elongated body portion 32 is configured and dimensioned to receive actuator member 66 for reciprocal motion therein.

Needle deployment assembly 36 includes a pair of needle carriers 50 and 52. Needle carriers 50 and 52 are slidably associated with respect to camming slots 54 and 56, respectively, formed on leg portions 58 and 60 of clevis 62 at distal end 64 of longitudinally slidable actuator member 66. These needle carriers 50 and 52 are movable between a retracted and deployed position by means of the relative reciprocal motion of tubular body 32 and actuator member 66.

Needle carrier 50 is disposed in an angular groove 69 on one side of elongated plug member 68 and needle carrier 52 is disposed in a corresponding angular grove 71 on the other side thereof. Needle carrier 52 is operatively assembled with actuator member 66 by inserting pin 70 in hole 72 which is formed near edge 74 of needle carrier 52 such that a portion of pin 70 protrudes from hole 72. Edge 74 is located opposite edge 76 which has needle holder portion 78 (FIG. 5) disposed therealong. The protruding portion of pin 70 is then fitted into camming slot 56 formed in extended leg portion 60. Elongated plug member 68, having boss 80 (FIG. 7) formed parallel to the side walls of and positioned on the bottom wall of transverse diagonal groove 82, is then fitted over needle carrier 52 such that boss 80 cooperates with slot 84 formed in needle carrier 52.

Needle carrier 50 is placed in transverse diagonal groove 86 formed in elongated plug member 68 such that slot 88 fits over and cooperates with boss 90 (FIG. 7). Bosses 80 and 90 are preferably elongated raised portions formed in the seating surface of their respective transverse diagonal grooves 82 and 86 which are parallel to the side walls defining the grooves. The combination of the side walls of grooves and the bosses acting as a keyway for slots 84 and 88, forces needle carriers 50 and 52 to travel in a path parallel to the side walls of the grooves. Pin 92 is placed in hole 94 formed near edge 96 of needle carrier 50 such that a portion of pin 92 protrudes from hole 94. Edge 96 is located opposite edge 98 which has needle holder portion 100 (FIG. 9) disposed therealong. Leg portion 58 having camming slot 54 formed thereon, (shown in phantom lines as a minor image of camming slot 56, see also FIGS. 4 and 8) is positioned over needle carrier 50 such that the protruding portion of pin 92 fits into camming slot 54. Leg portion 58 is attached to surface 102 of longitudinally slidable actuator member 66 by using any suitable bonding method and materials such as glue or epoxy.

Leg portion 60 is preferably formed integrally with actuator member 66, whereas, leg portion 58 is preferably detached to facilitate assembly of the remainder of the components contained in distal end 38 of elongated tubular body 32.

In other embodiments leg portions 58 and 60 may both be detached from actuator member 66 or they may both be formed integrally therewith. In the latter case, flexible materials may be utilized in the construction of actuator member 66 such that leg portions 58 and 60 may be temporarily spread to insert the needle carriers in their appropriate positions.

FIGS. 1-3 illustrate how the suture is mounted in place. In one preferred embodiment, double armed suture 104 is utilized and has needles 22 and 24 attached one to either end of a length of suture thread 106 which is best illustrated in FIG. 3. To accommodate suture thread 106, longitudinal grooves 108 and 110 are provided one on either side of actuator member 66 (See also FIG. 12). Groove 108 extends along leg portion 58 and is denoted thereon by reference numeral 108b.

Referring more specifically to the double armed suture 104, needle 22 is mounted in needle holder portion 100 (FIG. 9) preferably in the form of a clip which releasably holds needle 22 therein. Suture thread 106 is threaded towards distal end 112 of elongated plug member 68, into slot 114 and out of transversely intersecting slot 110a which is aligned with groove 110 (FIG. 12). A first loop 116 is formed in suture thread 106 such that loop 116 is positioned in groove 110 with the end of the loop preferably extending just beyond proximal end 118 of actuator member 66. As can be seen suture thread 106 extends back toward distal end 112 of elongated plug member 68, back into slot 110a traversing distal end 112 and out slot 108a. A second loop 120, is formed in suture thread 106 such that loop 120 is positioned in grooves 108b and 108. The end of loop 120 also extends just beyond end 118 of elongated member 66. Suture thread 106 extends back toward distal end 112 of elongated plug member 68 back into slot 108a and out of transversely intersecting slot 115. Needle 24 is mounted in needle holder portion 78 (FIG. 9) on needle carrier 52.

A resilient annular member such as O-ring 122 is positioned over proximal end 118 of actuator member 66 and is seated in annular groove 124 formed near proximal end 118. Preferably, O-ring 122 is positioned over loops 116 and 120 so as to hold them seated in grooves 110 and 108b, 108, respectively.

Actuator member 66 and connecting rod 126 are joined by pin 128 inserted into holes 130 and 132 formed in actuator member 66 and the distal end of connecting rod 126, respectively. Actuator member 66 is initially positioned with needle carriers 50 and 52 retracted into elongated tubular body portion 32. In this retracted position, (non-deployed) loops 116 and 120 of suture 104 extend through holes 134 and 136, respectively. Movable handle portion 30 is attached to connecting rod 126 by pin 138 inserted into hole 140 and a corresponding hole (not shown) formed in the proximal end of connecting rod 126.

The operation of instrument 20 will now be discussed with reference to FIGS. 4-12. FIGS. 4-7 illustrate closure device 20 in the closed position with the needles retracted, whereas, FIGS. 8-12 illustrate closure device 20 in the open position with needles 22 and 24 fully extended. Referring initially to FIGS. 4-7, needle carriers 50 and 52 are shown retracted completely within elongated tubular body 32. In this position, movable handle 30 is in its distal-most position. In the closed or retracted position of FIG. 4 pin 92 is shown at point A in camming slot 54. Suture thread 106 is shown disposed in elongated groove 108 and held therein by O-ring 122 which is seated in annular groove 124. Loop 120 extends out from hole 136 shown in phantom lines.

FIG. 5 illustrates the relative positioning of needle carriers 50 and 52 within elongated tubular body 32. FIG. 6 shows the relative positioning of suture 106 in the slots provided at distal end 112 of elongated plug member 68. FIG. 7 illustrates the interfitting of boss members 80 and 90 with slots 84 and 88, respectively.

Referring to FIGS. 8-12, the operation of deploying needle carriers 50 and 52 will now be described. To deploy needles 22 and 24, movable handle portion 30 is pulled to its proximal-most position as illustrated in FIG. 1. As movable handle 30 is pulled proximally, camming slots 54 and 56, formed on leg portions 58 and 60, also move proximally. As a combined result of: 1) needle carriers 50 and 52 being disposed in transverse diagonal grooves 86 and 82 of elongated plug member 68 and guided by boss members 90 and 80 cooperating with slots 88 and 84 (FIG. 7) and 2) pins 92 and 70 being guided by camming slots 54 and 56, such that pins 92 and 70 travel from points A to points B respectively therein, needle carriers 50 and 52 are urged outwardly from elongated tubular body 32 through longitudinal slots 142 and 144 formed at distal end 38 thereof.

Figures 8, 9:
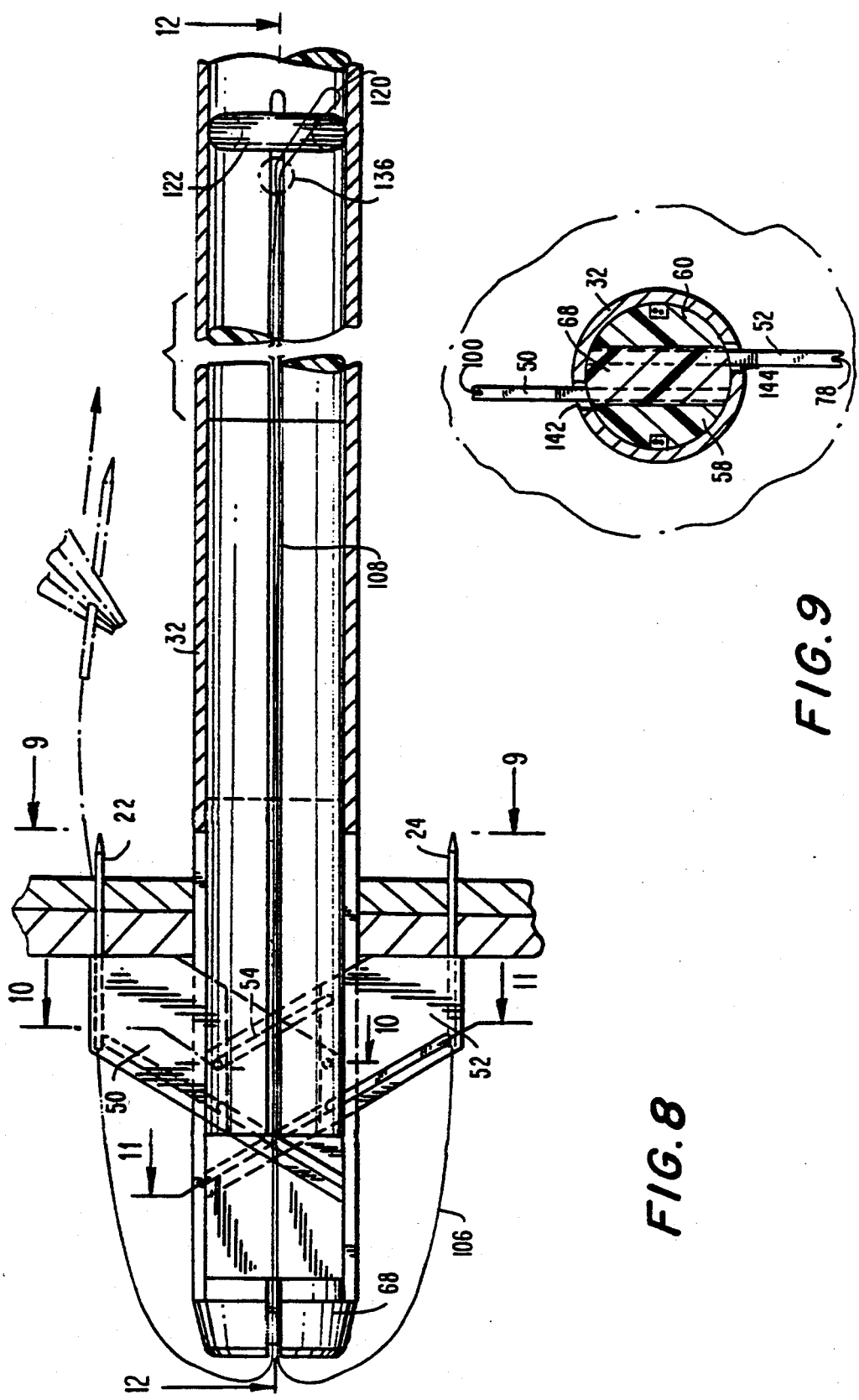
FIG. 8 is a cross-sectional view taken along line 8—8 of FIG. 1.
FIG. 9 is a cross-sectional view taken along line 9—9 of FIG. 8.

As needle carriers 50 and 52 are deployed, O-ring 122 moves on the proximally side of holes 134 and 136 thereby releasing suture thread 106. The entire instrument 20 can then be pulled proximally until needles 22 and 24 are through the fascia. Suture needles 22 and 24 pulled from needle carrier 50 and 52, respectively, as illustrated in FIG. 8 in phantom lines.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above but not limited thereto, are to be considered within the scope of the invention.

What is claimed is:

1. An instrument for closing puncture wounds comprising:
   a) a handle assembly having a stationary portion and a movable portion;
   b) an elongated portion having a longitudinal axis, said elongated portion attached at a proximal end thereof to said stationary portion of said handle assembly; and
   c) surgical needle deploying means associated with said elongated portion, said needle deploying means including:
      i. an actuator member having a proximal end operably connected to said movable portion of said handle assembly and a distal end disposed adjacent a distal end of said elongated portion, said actuator member being slidable between a first position and a second position;
      ii. at least one needle carrier assembly mounted to said actuator member adjacent said distal end thereof, said at least one needle carrier assembly being slidable relative to said actuator member upon movement thereof, wherein said at least one needle carrier assembly is movable between a retracted position substantially within said elongated portion and an extended position disposed a predetermined distance from said longitudinal axis spaced radially from said longitudinal axis and whereby said at least one needle carrier assembly is substantially outside of said elongated portion; and
      iii. a needle positioned within said needle carrier.

2. An instrument for closing puncture wounds according to claim 1 wherein said actuator member includes at least one camming surface formed in said distal end which is slidably engaged by said at least one needle carrier assembly such that upon longitudinal reciprocal movement of said actuator member said at least one needle carrier assembly is urged between said retracted position and said extended position.

3. An instrument for closing puncture wounds according to claim 1 further comprising means associated with said distal end of said elongated portion for aligning said at least one needle carrier relative to said actuator member.

4. An instrument for closing puncture wounds according to claim 3 wherein said aligning means includes an elongated plug member mountable adjacent said distal end of said elongated portion, said plug member having at least one substantially transverse groove defined by at least one wall portion, said wall portion being configured and dimensioned for receiving said at least one needle carrier such that said at least one needle carrier assembly is slidable within said groove between said retracted position and said extended position.

5. An instrument for closing puncture wounds according to claim 4 wherein said wall portion is provided with a boss portion longitudinally aligned with a predetermined direction of travel of said at least one needle carrier assembly for cooperating therewith such that said at least one needle carrier assembly is guided by said boss portion in said predetermined direction of travel.

6. An instrument for closing puncture wounds according to claim 5 wherein said at least one needle carrier assembly is provided with a slot thereon such that said slot cooperates with said boss portion of said substantially transverse groove of said plug member.

7. An instrument for closing puncture wounds according to claim 1 wherein said at least one needle carrier assembly includes a pair of needle carrying assemblies.

8. An instrument for closing puncture wounds according to claim 7 wherein said pair of needle carring assemblies are diametrically opposed with respect to each other.

9. An instrument for closing puncture wounds according to claim 1 wherein said actuator member has means disposed thereon for receiving and retaining a length of suture between said actuator member and said elongated portion.

10. An instrument for closing puncture wounds according to claim 9 wherein said suture receiving and retaining means includes at least one elongated channel disposed along said actuator member such that a length of suture may be received and retained within said channel and carried therein, between said elongated portion and said actuator member.

11. An instrument for closing puncture wounds according to claim 10 wherein said suture receiving and retaining means further includes at least one retaining member associated with said actuator member adjacent said at least one elongated channel such that a length of suture disposed in said channel is removably held therein.

12. An instrument for closing puncture wounds according to claim 11 wherein said at least one retaining member is a resilient annular member.

13. An instrument for closing puncture wounds according to claim 12 wherein said actuator member includes an annular groove formed therein adjacent said proximal end such that said at least one retaining member fits within said groove.

14. An instrument for closing puncture wounds according to claim 1 wherein said elongated portion is configured and dimensioned for insertion into the body through a trocar cannula.

15. Instrument for closing puncture wounds comprising:
   a) elongated housing having a longitudinal groove adjacent a distal end thereof;
   b) at least one needle deployably mounted and disposed within said groove of said housing; and
   c) means associated with said housing for operably deploying said needle between a retracted position substantially within said groove and an extended position radially spaced from said groove, at least one needle carrier member for replaceably receiving said at least one needle therein, said at least one needle carrier member slidably disposed on said needle deploying means and movable between a first position and a second position spaced a predetermined distance from said longitudinal axis.

16. An instrument for closing puncture wounds according to claim 15, further comprising a handle assembly including a stationary handle portion securely attached to a proximal end of said elongated housing and a slidable handle portion operatively associated with said needle deploying means.

17. An instrument for closing puncture wounds according to claim 15, wherein said needle deploying means includes a camming pin engageable with said at least one needle carrier member for deployment thereof.

18. An instrument for closing puncture wounds according to claim 17, wherein said needle deploying means further includes an actuator member operatively associated with said pin engaging said actuator member.

19. An instrument for closing puncture wounds according to claim 18, wherein said actuator member defines an elongated slot for slidably receiving said pin and said pin is fixedly attached to said at least one needle carrier member.

20. An instrument for closing puncture wounds according to claim 15, wherein said needle deploying means includes a elongated actuator member movable relative said elongated housing and an aligning member fixed relative to said elongated housing and operatively associated with said elongated actuator member to facilitate movement of said at least one needle carrier member between said first and second positions.

21. An instrument for closing puncture wounds according to claim 20, wherein said elongated actuator member defines a cam slot operatively associated with said at least one needle carrier member.

22. An instrument for closing puncture wounds comprising:
   a) a handle assembly having a stationary portion and a movable portion;
   b) an elongated portion attached at a proximal end thereof to said stationary portion of said handle assembly;
   c) needle deploying means associated with said elongated portion, said needle deploying means including:
      i. an actuator member having a proximal end operably connected to said movable portion of said handle assembly and a distal end disposed adjacent a distal end of said elongated portion, said actuator member being slidable between a first position and a second position; and
      ii. at least one needle carrier assembly mounted adjacent said distal end of said actuator member, said at least one needle carrier assembly being movable relative to said actuator member upon movement thereof, wherein said at least one needle carrier assembly is movable between a retracted position substantially within said elongated portion and an extended position substantially outside said elongated portion; and
   d) at least two elongated grooves associated with said actuator member, said grooves being dimensioned to accommodate a suture.

* * * * *